United States Patent [19]

Lemin et al.

[11] 4,017,630

[45] Apr. 12, 1977

[54] CERTAIN DIPHENYLALKANOAMIDES USED AS BIRD AND MURINE REPELLENTS

[75] Inventors: Alan J. Lemin, Plainwell; Paul W. O'Connell, Kalamazoo, both of Mich.

[73] Assignee: The Upjohn Company, Kalamazoo, Mich.

[22] Filed: Nov. 29, 1974

[21] Appl. No.: 528,216

Related U.S. Application Data

[63] Continuation of Ser. No. 64,575, Aug. 17, 1970, abandoned.

[52] U.S. Cl. .............................. 424/267; 424/274; 424/324
[51] Int. Cl.$^2$ .......................................... A01N 9/22
[58] Field of Search .................. 424/274, 265, 324

[56] References Cited

OTHER PUBLICATIONS

Moffett, Ct. 21, J.A.C.S. 79, pp. 4451–4465, (1957).

*Primary Examiner*—Leonard Schenkman
*Attorney, Agent, or Firm*—Martin B. Barancik; Carl A. Randles, Jr.

[57] ABSTRACT

Animals, especially birds and murine pests, are repelled by γ- or ω-amino-α,α-diphenylalkanoamides, their acid addition and quaternary ammonium salts, their N-oxides, and acid addition salts of the N-oxides. The active agents can be coated on grains in order to repel animals especially birds. Animal pest damage to mature crops for harvest and newly planted seeds is prevented.

21 Claims, No Drawings

CERTAIN DIPHENYLALKANOAMIDES USED AS BIRD AND MURINE REPELLENTS

This is a continuation of pending application Ser. No. 64,575 filed on Aug. 17, 1970, and now abandoned.

SUMMARY OF THE INVENTION

This invention pertains to a new method and to new formulations for repelling animals. The invention is more particularly directed to a new method and new formulations for repelling animals from prospective, available foods and from habitats. Still more particularly, the invention is directed to the new method and formulations using $\gamma$- or $\omega$-amino-$\alpha,\alpha$-diphenylalkanoamides.

The animal repellent $\gamma$- or $\omega$-amino-$\alpha,\alpha$-diphenylalkanoamides of this invention are known compounds. A general structural formula as the free base form is as follows:

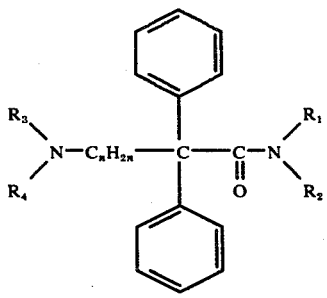

I wherein $R_1$ and $R_2$ are independently selected from the class consisting of hydrogen, and lower-alkyl of from 1 to 4 carbon atoms, inclusive; $n$ is the integer 2 or 3; $R_3$ and $R_4$ are independently selected from the class consisting of lower-alkyl of from 1 to 4 carbon atoms, inclusive, alkenyl of 3 or 4 carbon atoms; and $R_3$ and $R_4$ taken together with the coupled

atom form a saturated heterocyclic amino group of from 5 to 7 ring atoms, inclusive, having a total of not more than 10 carbon atoms. The acid addition salts, quaternary ammonium salts, N-oxides (including acid addition salts of N-oxides) preparable from the free base compounds of Formula 1 are active and useful in the new method for repelling animals in accordance with this invention. In the practice of the method a specific active compound can be formulated and used, or a mixture of two or more active compounds can be formulated and used.

DETAILED DESCRIPTION OF THE INVENTION

The numerous and varied animals that, in many areas, coexist on this earth indicate a Natural Law of competition for survival. Man has become a dominant factor in this competition, and more and more seeks to change the interrelationships of the diverse animals in order to satisfy his own desires. One of man's primary needs is food, and animals compete with man for the food produced on the earth. Animals also compete with man for space, and sometimes interfere with man's aesthetic values. Birds crowd into suitable roosting and nesting sites, and frequent the air space around airports; rodents undermine the foundations of buildings; gnaw holes in wood, fabrics, and paper; and both birds and rodents are carriers of pathogenic microorganisms that sometimes endanger the health of men.

So man in his dominant character tries to modify the competition. He ever increases the part of the earth that he possesses and from which he excludes other animals to a greater or lesser degree. Competing animals have been excluded from man's environs by killing them. Some more tolerant modes of exclusion were by frightening the animals away and by protective barriers. Now man is devising subtle chemical barriers that repel the animals, and cause them to avoid a competitive situation. This invention pertains to a newly discovered repellent action of $\gamma$- or $\omega$-amino-$\alpha,\alpha$-diphenylalkanoamides.

The compounds as generally identified as free bases in Formula 1, above, are repugnant to animals. Animals seem to dislike the taste of the compounds, although a scent repugnancy might be operating also. This repugnancy was initially observed in birds, but has now been observed in rodents, particularly murine pests, especially mice.

In accordance with the invention, one of the pure compounds of the class contemplated, a mixture of two or more compounds, or formulations thereof with other materials can be applied to objects or a situs and animals are repelled. These various forms are designated an "active agent" of the invention. Birds will avoid foods coated or impregnated with an active agent of the invention, and they can be repelled from roosting or nesting sites. Rodents are also repelled from, e.g., foods, fabrics, and papers coated or impregnated with an active agent, and they avoid habitats treated with an active agent.

Illustratively, wild mice provided a choice of food treated with $\gamma$-(2-methyl-1-pyrrolidinyl)-$\alpha,\alpha$-diphenylbutyramide and food not so treated were repelled by the treated food when the concentration of compound was 2.5, 0.5, and 0.1 percent. The degree of repellency was significant at each concentration according to analyses of probabilities. When similar wild mice were given a treated food on a no choice basis (eat or go hungry) the 2.5 percent concentration was significantly repellent.

Accordingly the active agents according to the invention can be mixed with, affixed to or incorporated in prospective, available foods and mice will be repelled. Seed grains, grain crops, other horticultural and agronomic crops, and other calorific foods can thus be protected from rodent damage. By the phrase calorific foods is meant an energy producing food sought out and utilized by animals, particularly birds and murine pests. Packaging materials can also be protected from rodent damage.

Birds have been found to be especially susceptible to the repellency of $\gamma$- or $\omega$-amino-$\alpha,\alpha$-diphenylalkanoamides according to this invention. In one field test, three batches of seed sweet corn were planted. One batch was not treated with an active agent. A second batch was treated so as to have 0.5 percent (of seed weight) of $\gamma$-(2-methyl-1-pyrrolidinyl)-$\alpha,\alpha$-diphenylbutyramide. A third batch was treated with 3.0 percent by weight of the compound. The active agent was in the form of a 99.5 percent dust.

These batches of treated and untreated seed sweet corns were planted on three-acre plots separated by acreages of equal size and replicated on opposite sides of a swamp known to be a habitat and roosting site for blackbirds. Twenty-four randomly selected subunits, each containing approximately 200 seeds, were observed for bird damage in each 3-acre plot. Destruction in each subunit was determined daily, from planting time until the corn plants were about 4 inches tall.

Blackbirds destroyed 3,341 seeds and seedlings in the untreated plots; but the treated plots were damaged only to the extent of 109 and 95 seeds and seedlings, respectively. The percentage losses were about 53 percent and 2 percent, respectively. Within 5 days after planting, the treated plots were substantially free from foraging blackbirds. In contrast, feeding activity was heavy and continuous in the untreated fields for at least 10 days after planting.

The effectiveness of the γ- or ω-amino-α,α-diphenylalkanoamides of this invention as repellents for birds is further established by determination of the concentrations needed in a feed in order to reduce food intake 50 percent. These $R_{50}$ values, expressed as percentage by weight, are approximately as follows for γ-(2-methyl-1-pyrrolidinyl)-α,α-diphenylbutyramide:

Common Grackles (*Quiscalus quiscula*): .056
House Sparrows (*Passer domesticus*): .261
Red-winged Blackbirds (*Agelauis phoeniceus*): .091
Ringneck Pheasant (*Phasianus colchicus*): .178
California Valley Quail (*Lophortyx californicus*): .178
Japanese Quail (*Coturnix coturnix japonica*): .180

Other compounds of Formula 1 give the same values with some variations. For example, the $R_{50}$ value for γ-(2-methyl-piperidino)-α,α-diphenylbutyramide is 0.056 percent (redwinged blackbirds). Other especially active compounds of Formula 1 are γ(2,5-dimethyl-1-pyrrolidinyl)-α,α-diphenylbutyramide hydrochloride,
γ-piperlidino-α,α-diphenylbutyramide N-oxide,
γ-(2,5-dimethyl-1-pyrrolidinyl)-α,α-diphenylbutyramide,
γ-(dimethylamino)-α,α-diphenylvaleramide sulfate,
γ-(2-methyl-1-piperidino)-α,α-diphenylbutyramide hydrochloride,
γ-piperidino-α,α-diphenylbutyramide hydrochloride, Still other representative γ- or ω-amino-α,α-diphenylalkanoamide animal repellent compounds according to this invention include:

γ-diethylamino-α,α-diphenyl-N-methylbutyramide hydrochloride,
γ-diisopropylamino-α,α-diphenyl-N-methylbutyramide hydrochloride,
γ-di-n-butylamino-α,α-diphenyl-N-methylbutyramide hydrochloride,
γ-diallylamino-α,α-diphenyl-N-methylbutyramide hydrochloride,
γ-di-2-butenylamino-α,α-diphenylbutyramide hydrochloride (also γ-hexamethyleneimino- ... ),
ω-(2-methyl-1-pyrrolidinyl)-α,α-diphenylvaleramide,
γ-dimethylamino-α,α-diphenyl-N-methylvaleramide,
γ-dimethylamino-α,α-diphenyl-N-isopropylvaleramide hydrochloride [also γ-(2-isohexyl-1-pyrrolidinyl)- ... ],
γ-(2-methyl-1-pyrrolidinyl)-α,α-diphenylbutyramide methobromide,
γ-dimethylamino-α,α-diphenyl-N-tert.butylvaleramide methobromide, and
γ-(piperidino)-α,α-diphenylbutyramide methobromide.

The compounds of Formula 1 including the specific ones named above can be used at various concentrations varying from about 0.01 to about 0.02 percent up to about 5 percent or more, or in amounts of about 0.1 mg. to about 1 g. for repelling birds and animals.

The compounds of Formula 1, their acid addition and quaternary ammonium salts, their N-oxides, and acid addition salts of N-oxides are prepared according to the procedures described by Moffett and Aspergren, J.A.C.S. 79, pp. 4451–4456 (1957); Moffett, Aspergren, and Speeter, J.A.C.S. 79, pp. 4457–4462 (1957); and Moffett and Aspergren, J.A.C.S. 79, pp. 4462–4465 (1957).

Representative mineral acid addition salts include the hydrochlorides, the hydrobromides, the hydroiodides, the sulfates, the phosphates, the hexafluorophosphates, the nitrates, the arsenates and the fluosilicates. Representative organic acid addition salts are the acetates, the propionates, the benzoates, the salicylates, the glycolates, the succinates, the nicotinates, the tartrates, the maleates, the malates, the oxalates, the pamoates, the methanesulfonates, the dodecylbenzenesulfonates, the picrates, the arsanilates, and the lactates.

Representative quaternary ammonium salts include the alkyl halide salts, e.g., methochlorides, methobromides, methiodides, ethochlorides, isopropobromides, and the like; alkenyl halides, e.g., allyl chloride, crotyl bromide, and the like; alkyl nitrate salts; alkyl sulfate salts; alkyl phosphate salts; and alkyl aryl sulfonate salts.

The active repellents of this invention, the γ- or ω-amino-α,α-diphenylalkanoamides of Formula 1 are effective in their pure form, as mixtures of pure compounds, or as formulations with a diluent carrier with or without adjuvants. A diluent carrier is frequently used in order to extend the active agent and thus facilitate use or application of concentrations of active compound consistent with practical economies.

A diluent carrier can be liquid, a dispersible solid, or a combination of liquid and solid. Accordingly, the formulation embodiment of the invention contemplates solutions of the active compounds in a solvent, suspensions, substantially homogeneous powders, pastes, ointments, granules, emulsions, and other forms useful and known to those skilled in the art.

The free base γ- or ω-amino-α,α-diphenylalkanoamides active compounds of this invention are not soluble in water, but are soluble in various organic liquids, for example, ethers, e.g., diethyl ether, alcohols, e.g., ethanol, ketones, e.g., acetone, cyclohexanone, and liquid chlorinated hydrocarbons, e.g., methylene chloride. On the other hand, the salts embodiments of the active compounds are variably soluble in water and other solvents and can be used for appropriate practice of the method of this invention.

In general, suitable solvents include aromatic hydrocarbons, for example, benzene, toluene, xylenes, and naphthalenes, chlorinated aromatic hydrocarbons, for example, chlorobenzenes; paraffins, for example, petroleum fractions; animal and vegetable oil, for example, soybean oil, linseed oil, safflower oil, olive oil, lanolin; ethanolamine; dimethylformamide; dimethylsulfoxide; and the like.

Dispersible solid carriers that can be used for preparing substantially homogeneous powders according to the invention include China clay and bentonite, minerals in the natural state such as talc, pyrophyllite, quartz, diatomaceous earth, fuller's earth, chalk, and rock phosphate, and the chemically modified minerals such as washed bentonite, precipitated calcium phosphate, precipitated calcium carbonate, precipitated calcium silicate, and colloidal silica.

A preferred substantially homogeneous powder in accordance with this invention is one comprising a dispersible powder as indicated above and a surfactant. The surfactant aids in the suspendability of the solid particles (powder) in water which is the common liquid dispersible carrier of agricultural practice. It also aids in the spreading characteristics of an aqueous formulation when applied to a surface. These preferred formulations are called wettable powders by those skilled in the art. Such wettable powders can be prepared having a wide range of concentrations of active ingredient. Concentrations can range from about 5 percent to about 90 percent (by weight) of active ingredient. Other concentrations can be used of course, but the objectives of economic practice of the invention will be satisfied in general by wettable powders having concentrations of about 20 percent to about 50 percent.

Representative surfactants useful for preparing wettable powder formulations of this invention include alkyl sulfates and sulfonates, alkyl aryl sulfonates, sulfosuccinate esters, polyoxyethylene sulfates, polyoxyethylene-sorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. The preferred class of surfactants includes blends of sulfonated oils and polyalcohol carboxylic acid esters (Emcol H-77), blends of polyoxyethylene ethers and oil-soluble sulfonates (Emcol H-400), blends of alkyl aryl sulfonates and alkyphenoxy polyethoxy ethanols (Tritons X-151, X-161, and X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul N$_4$S). It will be understood, of course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1 per cent or less. The dispersible powder compositions can be formulated with a mixture of surfactants of the types indicated if desired.

The wettable powders are utilized in the practice of the invention by dispersing in water for application to an object or situs from which susceptible animals are to be repelled. An aqueous spray can be applied to grain fields just prior to harvest, or to horticultural, viticultural and silvicultural crops, for example, cherry orchards, vineyards, conifers, and to buds of flowering fruit trees for repelling birds. Aqueous sprays can also be directed into trees comprising a roosting site in order to repel the birds and cause them to congregate an another roost location more compatible with man's interests.

A suitable dispersible powder formulation is obtained by blending and milling 327 lbs. of Georgia Clay, 4.5 lbs. of isooctylphenoxy polyethoxy ethanol (Triton X-100) as a wetting agent, 9 lbs. of a polymerized sodium salt of substituted benzoid long-chain sulfonic acid (Daxad 27) as a dispersing agent, and 113 lbs. of the active ingredient. The resulting formulation have the following percentage composition (parts herein are by weight unless otherwise specified):

Active ingredient: 25%
Isooctylphenoxy polyethoxy ethanol: 1%
Polymerized sodium salt of substituted benzoid long-chain sulfonic acid: 2%
Georgia Clay: 72%

This formulation, when dispersed in water at the rate of 10 lbs. per 100 gals., gives a spray formulation containing about 0.3% (3000 ppm) active ingredient which can be applied to trees, buildings, grain fields, or habitats of animals.

If desired, dispersants such as methyl cellulose, polyvinyl alcohol, sodium ligninsulfonates, and the like can be included in the dispersible powder formulations of this invention. Adhesive or sticking agents such as vegetable oils, naturally occurring gums, casein, and others can also be included. Corrosion inhibitors such as epichlorohydrin and anti-foaming agents such as stearic acid can also be included.

The active agent repellents of this invention can be applied to seeds, grain fields, roosting sites, objects or habitats in order to repel animals by using aqueous sprays prepared from a concentrated solution of the active agents. In accordance with this embodiment of the invention, an active agent (particularly the free bases) are preferably dissolved in a suitable inert organic solvent carrier. Advantageously, the solvent carrier is immiscible with water so that an emulsion of the solvent carrier in water can be prepared. If, for example, a water-miscible solvent carrier such as ethanol is used the solvent carrier will dissolve in the water and any excess $\gamma$- or $\omega$-amino-$\alpha$,$\alpha$-diphenylalkanoamides will be thrown out of solution. In an oil-in-water emulsion, the solvent phase is dispersed in the water phase and the dispersed phase contains the active ingredient. In this way, uniform distribution of a water insoluble active ingredient is achieved in an aqueous spray. A solvent carrier in which the compounds are soluble is desirable so that relatively high concentrations of active ingredient can be obtained. Sometimes, one or more solvent carriers with or without a cosolvent can be used in order to obtain concentrated solutions of the active ingredient, the main consideration being to employ a water-immiscible solvent for the active ingredient that will hold the compound in solution over the range of concentration useful for repelling the animals.

The emulsifiable concentrates of the invention are prepared, therefore, by dissolving the active ingredient and a surfactant in a substantially water-immiscible solvent carrier (i.e., a solven carrier which is soluble in water to the extent of less than 2.5% by volume at temperatures of the order of 20° to 30° C.), for example, cyclohexanone, methyl propyl ketone, summer oils, ethylene dichloride, aromatic hydrocarbons such as benzene, toluene, and xylene, and high-boiling petroleum hydrocarbons such as kerosene, diesel oil, and the like. If desired, a cosolvent such as methyl ethyl ketone, acetone, isopropanol, and the like can be included with the solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed, if desired.

Advantageously, the concentration of active ingredient in the emulsifiable concentrates can range from about 5% to about 50% by weight, preferably from about 10% to about 40%. A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1 qt. of a 20% concentrate mixed with 40 gals. of water provides about 1200 ppm (parts per million) of active ingredient. In the same manner, more concentrated solutions of active ingredient can be prepared.

The concentrate compositions of the invention which are intended for use in the form of aqueous dispersions or emulsions can also comprise a humectant, that is to say, an agent which will delay the drying of the composition in contact with material to which it has been applied. Suitable humectants include glycerol, diethylene glycol, solublizied lignins, such as calcium ligninsulfonate, and the like.

EXAMPLE 1

A dispersible powder concentrate having the following percentage composition:
γ-(2-methyl-1-pyrrolidinyl)-α,α-diphenylbutyramide: 45.8%
Polymerized sodium salt of substituted benzoid long-chain sulfonic acid (Daxad 27): 9.2%
Kaolinite: 45.0% was prepared by mixing 250 gm. γ-(2-methyl-1-pyrrolidinyl)-α,α-diphenylbutyramide, 50 gm. of a polymerized sodium salt of substituted benzoid long-chain sulfonic acid (Daxad 27), and 245 gm. of kaolinite. The mixture was milled to a particle size ranging from 5 to 30 microns. It was suspended in 10 gals. of water, giving an aqueous spray containing about 6500 parts per million of active ingredient for application to seeds or grain fields for repelling birds.

EXAMPLE 2

An emulsifiable concentrate having the following percentage composition:
γ-(2,5-dimethyl-1-pyrrolidinyl)-α,α-diphenylbutyramide HCl: 15.0%
Technical alkyl naphthalene boiling at 238° to 293+ C. (Velsicol AR50): 19.7%
Xylene: 17.4%
Isopropyl alcohol: 17.4%
Ethylene dichloride: 25.4%
Blend of alkyl aryl sulfonates and alkylphenoxy polyethoxy ethanols (Triton X-151): 5.1% was prepared by mixing 15.0 lbs. of γ-(2,5-dimethyl-1-pyrrolidinyl)-α,α-diphenylbutyramide HCl, 19.7 lbs. of Velsicol AR50, 17.4 lbs. of xylene, 17.4 lbs. of isopropyl alcohol, 25.4 lbs. of ethylene dichloride, and 5.1 lbs. of Triton X-151.

6.67 lbs. of the concentrate mixed with 10 gals. of water gave a spray emulsion containing 11,000 ppm of γ-(2,5-dimethyl-1-pyrrolidinyl)-α,α-diphenylbutyramide HCl for application to seeds for repelling birds.

EXAMPLE 3

An emulsifiable concentrate having the following percentage composition:
γ-dimethylamino-α,α-diphenylvaleramide sulfate: 40.0%
Technical alkyl naphthalene boiling at 238° to 293° C. (Velsicol AR50): 13.7%
Xylene: 12.3%
Isopropyl alcohol: 11.3%
Ethylene dichloride: 17.7%
Blend of alkyl aryl sulfonates and alkylphenoxy polyethoxy ethanols (Triton X-151) 5.0% was prepared by mixing 40.0 lbs. of γ-dimethylamino-α,α-diphenylvaleramide sulfate, 13.7 lbs. of Velsicol AR50, 12.3 lbs. of xylene, 11.3 lbs. of isopropyl alcohol, 17.7 lbs. of ethylene dichloride, and 5.0 lbs. of Triton X-151.

1.67 lbs. of the concentrate mixed with 10 gals. of water gave a spray emulsion containing 8,000 ppm of α-dimethylamino-α,α-diphenylvaleramide sulfate for application to habitats or objects for repelling animals.

EXAMPLE 4

A wettable powder concentrate having the following percentage composition:
γ-piperidino-α,α-diphenylbutyramide N-oxide: 50%
Kaolinite clay (finely divided): 46%
Sodium salt of condensed mononaphthalene sulfonic acid (Lomar D): 4% was prepared by mixing 50 g. of γ-piperidino-α,α-diphenylbutyramide N-oxide, 46 g. of the kaolinite clay, and 4 g. of Lomar D. The mixture was milled to an average particle size of 5 to 30 microns, and can be used to coat seed grains.

EXAMPLE 5

The active agent γ-(2,5-dimethyl-1-pyrrolidinyl)-α,α-diphenylbutyramide hydrochloride is dissolved in a 40% solution of isopropyl alcohol in water and the solution is sprayed over grain sorghum while the grain is being tumbled and mixed. An amount of spray is applied so as to provide about 0.2% by weight of the active agent. After drying, the coated grain is spread over a seeded field in order to repel birds. A light spreading of about 4 quarts per acre in a band about 200 ft. wide particularly around the edges of large fields will repel hungry bird flocks.

The same repellent effect is obtained by dissolving one part γ-(2-methylpiperidino)-α,α-diphenylbutyramide hydrochloride and one part γ-(2-methyl-1-pyrrolidinyl)-α,α-diphenylbutyramide in the isopropyl alcohol.

Similarly, the free base compounds of the invention, their N-oxides, their quaternary ammonium salts, and N-oxide acid addition salts or mixtures thereof can be used as the active agents for the same repellent effect.

We claim:

1. A method of repelling birds and murine pests from prospective available foods which comprises coating the food or mixing with the food an effective amount of a compound of the formula

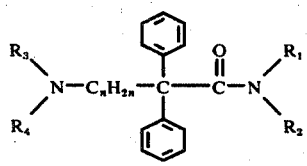

wherein $R_1$ and $R_2$ are independently selected from the group consisting of hydrogen and alkyl of one to four carbon atoms, inclusive, $n$ is 2 or 3, $R_3$ and $R_4$ are independently selected from the group consisting of alkyl of one to four carbon atoms, inclusive, alkenyl of three or four carbon atoms; and $R_3$ and $R_4$, when taken together with the nitrogen atom to which they are attached, form a saturated alicyclic ring containing four to six carbon atoms, said alicyclic ring carbons being unsubstituted or substituted with one or more alkyl groups, the total number of carbon atoms in the ring and alkyl substituents being not more than ten, an acid addition salt thereof, a quaternary ammonium salt thereof, an N-oxide thereof or an N-oxide acid addition salt thereof.

2. The method according to claim 1 wherein n is 2 and $R_1$ and $R_2$ are hydrogen.

3. The method according to claim 2 wherein $R_3$ and $R_4$ taken together with the N atom to which they are attached, form a saturated alicyclic ring containing four to six carbon atoms, said alicyclic ring carbons being unsubstituted or substituted with one or more alkyl groups, the total number of carbon atoms in the ring and alkyl substituents being not more than ten.

4. The method according to claim 3 wherein

is pyrrolidinyl.

5. The method according to claim 3 wherein the compound is a γ-(monolower-alkyl- or dilower-alkyl-1-pyrrolidinyl)-α,α-diphenylbutyramide.

6. The method according to claim 5 wherein the compound is γ-(2-methyl-1-pyrrolidinyl)-α,α-diphenylbutyramide.

7. The method according to claim 5 wherein the compound is γ-(2,5-dimethyl-1-pyrrolidinyl)-α,α-diphenylbutyramide.

8. The method according to claim 3 wherein

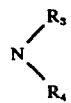

is piperidino.

9. The method according to claim 3 wherein the compound is a γ-(monolower-alkylpiperidino)-α,α-diphenylbutyramide.

10. The method according to claim 9 wherein the compound is γ-(2-methylpiperidino)-α,α-diphenylbutyramide.

11. A composition which comprises a calorific food having affixed thereto or mixed therewith a bird or murine pest repellent amount of a compound of the formula

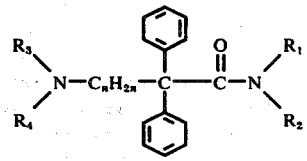

wherein $R_1$ and $R_2$ are independently selected from the group consisting of hydrogen and alkyl of one to four carbon atoms, inclusive, $n$ is 2 or 3, $R_3$ and $R_4$ are independently selected from the group consisting of alkyl of one to four carbon atoms, inclusive, alkenyl of three or four carbon atoms; and $R_3$ and $R_4$, when taken together with the nitrogen atom to which they are attached, form a saturated alicyclic ring containing four to six carbon atoms, said alicyclic ring carbons being unsubstituted or substituted with one or more alkyl groups, the total number of carbon atoms in the ring and alkyl substituents being not more than ten, an acid addition salt thereof, a quaternary ammonium salt thereof, an N-oxide thereof or an N-oxide acid addition salt thereof.

12. A composition according to claim 11 wherein $n$ is 2 and $R_1$ and $R_2$ are hydrogen.

13. A composition according to claim 12 wherein $R_3$ and $R_4$, taken together with the N atom to which they are attached, form a saturated alicyclic ring containing four to six carbon atoms, said alicyclic ring carbons being unsubstituted or substituted with one or more groups, the total number of carbon atoms in the ring and alkyl substituents being not more than ten.

14. A composition according to claim 13 wherein

is pyrrolidinyl.

15. A composition according to claim 13 wherein the compound is γ-(2-methyl-1-pyrrolidinyl)-α,α-diphenylbutyramide.

16. A composition according to claim 11 wherein the calorific food is a seed.

17. A composition according to claim 16 wherein the seed is corn.

18. A composition which comprises a calorific food having affixed thereto or mixed therewith from about 0.01 percent to about 5 percent by weight of a compound of the formula

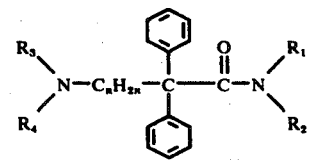

wherein $R_1$ and $R_2$ are independently selected from the group consisting of hydrogen and alkyl of one to four carbon atoms, inclusive, $n$ is 2 or 3, $R_3$ and $R_4$ are independently selected from the group consisting of alkyl of one to four carbon atoms, inclusive, alkenyl of three or four carbon atoms; and $R_3$ and $R_4$ when taken together with the nitrogen atom to which they are attached, form a saturated alicyclic ring containing four to six carbon atoms, said alicyclic ring carbons being unsubstituted or substituted with one or more alkyl groups, the total number of carbon atoms in the ring and alkyl substituents being not more than ten, an acid addition salt thereof, a quaternary ammonium salt thereof, an N-oxide thereof or an N-oxide acid addition salt thereof.

19. A composition according to claim 18 wherein the calorific food is an edible seed.

20. A composition according to claim 19 wherein the seed is corn seed having about 0.1 to about 2.5 percent of the compound.

21. A composition according to claim 20 wherein the compound is $\gamma$-(2-methyl-1-pyrrolidinyl)-$\alpha,\alpha$-diphenylbutyramide.

* * * * *